US012678578B2

(12) United States Patent
da Silva et al.

(10) Patent No.: US 12,678,578 B2
(45) Date of Patent: Jul. 14, 2026

(54) FOR OF WATER ACCUMULATION ON VENTILATOR AIRWAY CIRCUITS FROM AIRWAY PRESSURE AND FLOW

(71) Applicant: KONINKLIJKE PHILIPS N.V., Eindhoven (NL)

(72) Inventors: Ikaro Garcia Araujo da Silva, Cambridge, MA (US); Samer Bou Jawde, Cambridge, MA (US); Roberto Buizza, Cambridge, MA (US); Cornelis van Zon, Cambridge, MA (US); Isha Malekar, Cambridge, MA (US); Francesco Vicario, Cambridge, MA (US)

(73) Assignee: Koninklijke Philips N.V., The Netherlands (AG)

( * ) Notice: Subject to any disclaimer, the term of this patent is extended or adjusted under 35 U.S.C. 154(b) by 470 days.

(21) Appl. No.: 18/519,158

(22) Filed: Nov. 27, 2023

(65) Prior Publication Data
US 2024/0173500 A1 May 30, 2024

Related U.S. Application Data

(60) Provisional application No. 63/428,511, filed on Nov. 29, 2022.

(51) Int. Cl.
*A61M 16/00* (2006.01)

(52) U.S. Cl.
CPC ...... *A61M 16/026* (2017.08); *A61M 16/0003* (2014.02); *A61M 2016/0027* (2013.01); *A61M 2016/0033* (2013.01)

(58) Field of Classification Search
CPC ............... A61M 16/00; A61M 16/026; A61M 16/0003; A61M 16/024; A61M 16/0051;
(Continued)

(56) References Cited

U.S. PATENT DOCUMENTS

2012/0037159 A1* 2/2012 Mulqueeny ....... A61M 16/0003
128/204.23
2015/0202394 A1* 7/2015 Angelico .......... A61M 15/0051
128/204.23
(Continued)

FOREIGN PATENT DOCUMENTS

CN 109876262 A 6/2019
CN 111529848 A 8/2020
(Continued)

*Primary Examiner* — Rachel T Sippel
*Assistant Examiner* — Gwynneth L Howell
(74) *Attorney, Agent, or Firm* — Daniel H. Brean

(57) ABSTRACT

A method for automated detection of water accumulation in a ventilator, comprising: (i) a plurality of iterations of: calculating an airway pressure water accumulation index; calculating a flow water accumulation index; labeling, using a trained asynchrony detection algorithm, the single breath of the patient as synchronous or asynchronous, and ranking all of the input features based on an importance of each respective input feature to the synchronous or asynchronous determination; (ii) for the plurality of iterations; determining, a most frequent breath labeling, a most frequent most important input feature, and a most frequent most important input feature for each type of breath; and determining one or more of: (1) water accumulation and an action to remove the water accumulation; and (2) asynchrony due to a cause other than water accumulation, and an action to correct the asynchrony; and (iii) notifying a user of the determined action.

15 Claims, 10 Drawing Sheets

(58) Field of Classification Search
CPC .. A61M 2016/0027; A61M 2016/0033; A61M
2205/18; A61M 2205/3331; A61M
2205/502; A61M 2230/40; G16H 20/40;
G16H 40/60; G16H 40/63; G16H 40/67
See application file for complete search history.

(56) References Cited

U.S. PATENT DOCUMENTS

2021/0016035 A1*  1/2021  Euliano, II ........... A61B 5/7282
2021/0220587 A1    7/2021  Gholami

FOREIGN PATENT DOCUMENTS

CN       111905208  A    11/2020
WO      2020122739  A1    6/2020

* cited by examiner

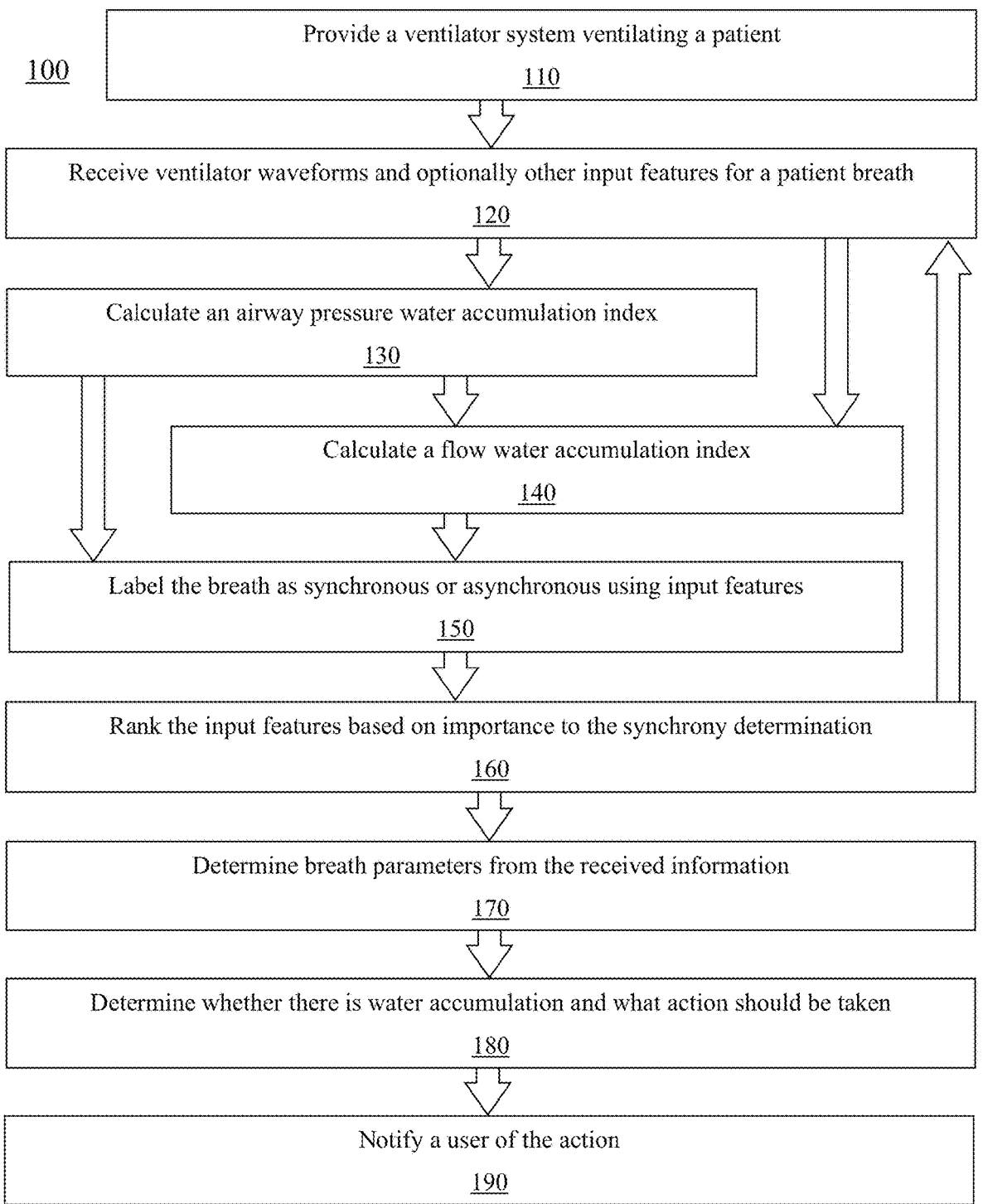

100

Provide a ventilator system ventilating a patient
110

Receive ventilator waveforms and optionally other input features for a patient breath
120

Calculate an airway pressure water accumulation index
130

Calculate a flow water accumulation index
140

Label the breath as synchronous or asynchronous using input features
150

Rank the input features based on importance to the synchrony determination
160

Determine breath parameters from the received information
170

Determine whether there is water accumulation and what action should be taken
180

Notify a user of the action
190

FOR OF WATER ACCUMULATION ON VENTILATOR AIRWAY CIRCUITS FROM AIRWAY PRESSURE AND FLOW

CROSS-REFERENCE TO RELATED APPLICATIONS

This patent application claims the priority benefit under 35 U.S.C. § 119(e) of U.S. Provisional Application No. 63/428,511, filed on Nov. 29, 2022, the contents of which are herein incorporated by reference.

FIELD OF THE INVENTION

The present disclosure is directed generally to methods and systems for automated analysis of water accumulation in a ventilator device.

BACKGROUND

Ventilators are widely used to treat patients with impaired lung function or respiratory failure, triggered by head injuries, stroke, lung conditions such as acute respiratory distress syndrome (ARDS), pneumonia, or chronic obstructive pulmonary disease (COPD), and a wide variety of other conditions. Ventilation is also regularly used in patients under general anesthesia.

As one example of ventilation application, approximately 800,000 patients receive mechanical ventilation therapy support in Intensive Care Units (ICUs) across the United States every year. While mechanical ventilators are designed to provide life-critical support to the patient, learning how to operate and tune the ventilator settings to complex patient conditions can be a daunting task to even the most experienced Intensivists and Respiratory Therapists.

A key component for identifying optimal settings on mechanical ventilators is the avoidance of what is known as patient-ventilator asynchrony (PVA). PVAs manifest by the ventilator and the patient operating "out-of-phase", or in conflict, with each other. PVAs are estimated to be present in as many as 88% of mechanically ventilated patients. The occurrence of PVAs has the potential to affect the outcome and quality of life of mechanically ventilated patients. Some of the potential risks and associated with PVAs that have been reported in the scientific literature are: (i) 3-fold increase in duration of ventilation; (ii) 8-fold increase in tracheostomy rate; and (iii) 2-fold increase in ICU length of stay.

PVA detection and resolution are active areas of research, and one critical cause of PVA is the accumulation of water due to accumulation of water condensate in the breathing circuit, which can increase auto-triggering (AT) and double triggering (DT) asynchronies. Water accumulation can pose a significant health risk to the patient by providing a place for microorganisms to grow and lead to healthcare-associated infections. And even if water accumulation does not cause asynchrony, the accumulation of water in the ventilator system can be harmful for the patient as well as the system itself.

SUMMARY OF THE INVENTION

Accordingly, there is a need for ventilator systems that monitor for and determine water accumulation in a ventilator device, as well as for ventilator systems that can determine, when asynchrony is present, whether that asynchrony is due to water accumulation.

The present disclosure is directed to inventive methods and systems for automated monitoring for, and detection of, water accumulation in a ventilator circuit. Various embodiments and implementations herein are directed to a ventilator system comprising a trained asynchrony detection algorithm. The system calculates an airway pressure water accumulation index and a flow water accumulation index, which are utilized as input features for the trained asynchrony detection algorithm. The output of the trained asynchrony detection algorithm is utilized to determine one or more of: (i) water accumulation in the ventilator circuit and an action to remove the water accumulation from the ventilator circuit; and (ii) asynchrony in the ventilator circuit due to a cause other than water accumulation, and an action to correct the asynchrony. The system then notifies a user of the determined action to remove the water accumulation from the ventilator circuit or the determined action to correct the asynchrony.

According to one aspect, a method for automated detection of water accumulation in a ventilator device utilized to ventilate a patient is provided. The method includes: (i) a plurality of iterations of: receiving, for a single breath of the patient, an airway pressure waveform and a flow waveform; calculating, using the received airway pressure waveform, an airway pressure water accumulation index; calculating, using the received flow waveform, a flow water accumulation index; labeling, using at least the calculated airway pressure water accumulation index and the calculated flow water accumulation index as input features to a trained asynchrony detection algorithm, the single breath of the patient as synchronous or asynchronous, wherein an asynchronous breath is further labeled as auto-triggered, double-triggered, ineffectively triggered, or another type of asynchrony; and ranking, by the trained asynchrony detection algorithm, all of the input features based on an importance of each respective input feature to the determination of the single breath of the patient as synchronous or asynchronous by the trained asynchrony detection algorithm, comprising at least a determination of a most important input feature; (ii) for the plurality of iterations; determining, by the trained asynchrony detection algorithm: (1) a most frequent breath labeling for the plurality of iterations, wherein the most frequent breath labeling is one of synchronous, auto-triggered, double-triggered, ineffectively triggered, or the other type of asynchrony; and (2) a most frequent most important input feature for the plurality of iterations; and (3) a most frequent most important input feature for each of the synchronous, auto-triggered, double-triggered, ineffectively triggered, and other type of asynchrony breath labels; and determining, by the trained asynchrony detection algorithm using the most frequent breath labeling for the plurality of iterations, the most frequent most important input feature for the plurality of iterations, and the most frequent most important input feature for each of the synchronous, auto-triggered, double-triggered, ineffectively triggered, and other type of asynchrony breath labels, one or more of: (1) water accumulation in the ventilator device and an action to remove the water accumulation from the ventilator device; and (2) asynchrony in the ventilator device due to a cause other than water accumulation, and an action to correct the asynchrony; and (iii) notifying a user via a user interface of the ventilator device, of the determined action to remove the water accumulation from the ventilator device or the determined action to correct the asynchrony.

According to an embodiment, receiving further comprises receiving at least one additional input feature from the ventilator device, and labeling the single breath of the patient as synchronous or asynchronous further comprises using the received at least one additional input feature by the trained asynchrony detection algorithm.

According to an embodiment, the at least one additional input feature from the ventilator device comprises one or more of an estimate of cardiogenic artifact within a breath, a ventilator setting, ventilator breathing circuit (e.g., single limb, dual limb, mask, etc.), excursion of patient effort, slope of patient effort in a pressure and/or flow channel, patient effort lowest/highest value in a pressure and/or flow channel around breath initiation, estimation of patient effort in an airway pressure channel, estimation of patient effort in a flow channel, estimate of intrinsic PEEP level, and estimate of patient respiratory mechanics (i.e., respiratory compliance and/or resistance).

According to an embodiment, the determined action to remove the water accumulation from the ventilator device or the determined action to correct the asynchrony is removal of accumulated water from the ventilator device.

According to an embodiment, the trained asynchrony detection algorithm determines water accumulation in the ventilator device, and the action to remove the water accumulation from the ventilator device, in the absence of asynchronous breaths of the patient.

According to an embodiment, determining a most frequent breath labeling for the plurality of iterations comprises determining, for the plurality of iterations, a percentage of each of the synchronous, auto-triggered, double-triggered, ineffectively triggered, or other type of asynchrony breath labels; and determining a most frequent most important input feature for the plurality of iterations comprises determining, for the plurality of iterations, a percentage of each of the input features.

According to an embodiment, calculating the airway pressure water accumulation index comprises: (i) standardizing the received airway pressure waveform, comprising subtracting a calculated airway pressure waveform mean and dividing the received airway pressure waveform by a calculated standard deviation of the airway pressure waveform; (ii) determining a waveform trend, comprising application of a median filter; (iii) computing an airway pressure waveform residue, comprising subtracting the determined waveform trend from the standardized airway pressure waveform; (iv) computing a standard deviation of the computed airway pressure waveform residue.

According to an embodiment, calculating the flow water accumulation index comprises: (i) standardizing the received flow waveform, comprising subtracting a calculated flow waveform mean and dividing the received flow waveform by a calculated standard deviation of the flow waveform; (ii) determining a waveform trend, comprising application of a median filter; (iii) computing a flow waveform residue, comprising subtracting the determined waveform trend from the standardized flow waveform; and (iv) computing a standard deviation of the computed flow waveform residue.

According to another aspect is a system for automated detection of water accumulation. The system includes: a ventilator device utilized to ventilate a patient, the ventilator device configured to provide an airway pressure waveform and a flow waveform for a single breath of the patient; a trained asynchrony detection algorithm; a processor configured to: (i) perform multiple iterations of: calculating, using the received airway pressure waveform, an airway pressure water accumulation index; calculating, using the received flow waveform, a flow water accumulation index; labeling, using at least the calculated airway pressure water accumulation index and the calculated flow water accumulation index as input features to the trained asynchrony detection algorithm, the single breath of the patient as synchronous or asynchronous, wherein an asynchronous breath is further labeled as auto-triggered, double-triggered, or ineffectively triggered; and ranking, by the trained asynchrony detection algorithm, all of the input features based on an importance of each respective input feature to the determination of the single breath of the patient as synchronous or asynchronous by the trained asynchrony detection algorithm, comprising at least a determination of a most important input feature; and (ii) for the plurality of iterations: determine, by the trained asynchrony detection algorithm: (1) a most frequent breath labeling for the plurality of iterations, wherein the most frequent breath labeling is one of synchronous, auto-triggered, double-triggered, or ineffectively triggered, and (2) a most frequent most important input feature for the plurality of iterations; and (3) a most frequent most important input feature for each of the synchronous, auto-triggered, double-triggered, and ineffectively triggered breath labels; and determine, by the trained asynchrony detection algorithm using the most frequent breath labeling for the plurality of iterations, the most frequent most important input feature for the plurality of iterations, and the most frequent most important input feature for each of the synchronous, auto-triggered, double-triggered, and ineffectively triggered breath labels, one or more of: (1) water accumulation in the ventilator device and an action to remove the water accumulation from the ventilator device; and (2) asynchrony in the ventilator device due to one or more causes other than water accumulation, and an action to correct the asynchrony; and a user interface configured to provide the determined action to remove the water accumulation from the ventilator device or the determined action to correct the asynchrony.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1 is a flowchart of a method for automated detection of water accumulation in a ventilator, in accordance with an embodiment.

DETAILED DESCRIPTION OF EMBODIMENTS

The present disclosure describes various embodiments of a ventilator system and method. More generally, Applicant has recognized and appreciated that it would be beneficial to provide a ventilator system and method for the automated monitoring for, and detection of, water accumulation in a ventilator circuit. For example, the ventilator system calculates an airway pressure water accumulation index and a flow water accumulation index, which are utilized as input features for a trained asynchrony detection algorithm. The output of the trained asynchrony detection algorithm is utilized to determine one or more of: (i) water accumulation in the ventilator circuit and an action to remove the water accumulation from the ventilator circuit; and (ii) asynchrony in the ventilator circuit due to a cause other than water accumulation, and an action to correct the asynchrony. The system then notifies a user of the determined action to remove the water accumulation from the ventilator circuit or the determined action to correct the asynchrony.

The ventilator system and method disclosed or otherwise envisioned herein provides numerous advantages over the prior art. Providing a ventilator system that enables the automated monitoring, detection, and notification of patient-ventilator asynchrony and/or water accumulation can shorten ventilation duration, prevent tracheostomies, and shorten hospitalizations. This significantly improves patient outcomes, and potentially saves lives.

For example, prior art systems fail to identify or estimate water accumulation in the ventilator circuit, such as from ventilator waveforms. Further, prior art systems fail to determine whether asynchrony is caused or not caused by this water accumulation, which is a vital component for the management and reduction of asynchrony. Thus, the methods and systems described or otherwise envisioned herein are critical as the detection of water accumulation aids in the management of asynchrony as well as in the reduction of healthcare associated infections caused by water accumulation.

According to an embodiment, the methods and systems described or otherwise envisioned herein utilize a water accumulation index to detect water accumulation and facilitate the automatic detection and resolution of double-triggering (DT) asynchrony and auto-triggering (AT) asynchrony caused by the water accumulation or possibly by other causes.

According to an embodiment, a DT asynchrony can be identified when there are two delivered breaths for a single patient effort. For example, a pressure signal may show high frequency oscillations due to water accumulating in the tubes of the ventilator. This causes a double-trigger where one patient effort (i.e., a drop in the patient effort signal) leads to more than one breath being delivered.

Figure 3:
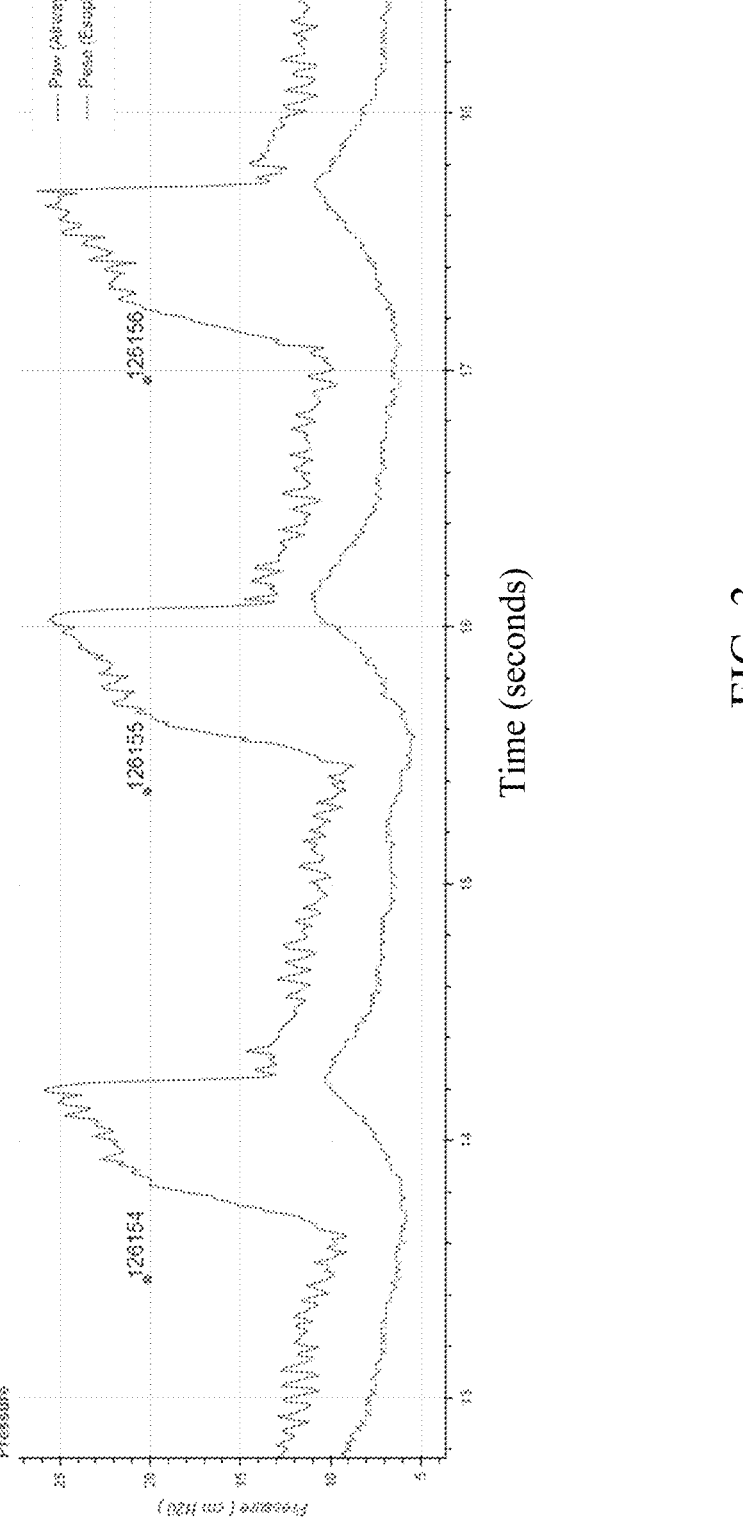
FIG. 3 is a graph of breath data showing possible auto-triggering (AT) asynchronies, in accordance with an embodiment.

According to an embodiment, an AT asynchrony can occur when there is significant amount of water (or secretion) accumulation present. This causes oscillations in the waveforms which are misrepresented as patient efforts leading to ventilator delivering an undesired breath. In other words, an AT asynchrony may be suggested by the delivery of a mechanical breath without any dip in esophageal pressure indicating patient effort. The high frequency oscillations in the waveforms suggest that the cause of auto-triggering is water (or secretion) accumulation. The methods and systems described or otherwise envisioned herein quantify the accumulation of liquid by quantifying the noise in waveforms, yielding a novel water accumulation index. For example, referring to FIG. 3, the first and last breaths are possible auto-triggering (AT) asynchronies, suggested by the delivery of a mechanical breath without any dip in esophageal pressure (lower line) indicating patient effort (as opposed to what can be observed in the second breath).

According to an embodiment, the water accumulation index is based on ventilator airway pressure and flow waveforms and is then analyzed by a trained algorithm to analyze whether water accumulation exists in the circuit. Water accumulation artifacts are typically considered noise and treated by ventilator systems as something that should be addressed by the ventilator's operator. However, operators may not be at the bedside to visually inspect the waveforms, and, even when present, they may not have the expertise to correctly identify the issue. Further, a significant amount of asynchrony events appear because of the noise caused by water accumulation in the waveforms that the ventilator normally uses to detect attempts from the patient to initiate a breath. This could increase the risk of damaging or reducing the performance of ventilator accessories (e.g., filters or exhalation cartridges). Further, the sources of asynchrony vary widely and are challenging for caregivers to identify whereas an automatic algorithm to automatically capture the cause has the potential to save a lot of debugging time and effort at the bedside. Therefore, as described or otherwise envisioned herein, water accumulation is treated as a signal of interest.

Referring to FIG. 1, in one embodiment, is a flowchart of a method 100 for automated detection of water accumulation in a ventilator circuit by a trained asynchrony detection algorithm of a ventilator system. The methods described in connection with the figures are provided as examples only, and shall be understood not to limit the scope of the disclosure. The ventilator system can be any of the systems described or otherwise envisioned herein. The ventilator system can be a single system or multiple different systems.

Figure 4:
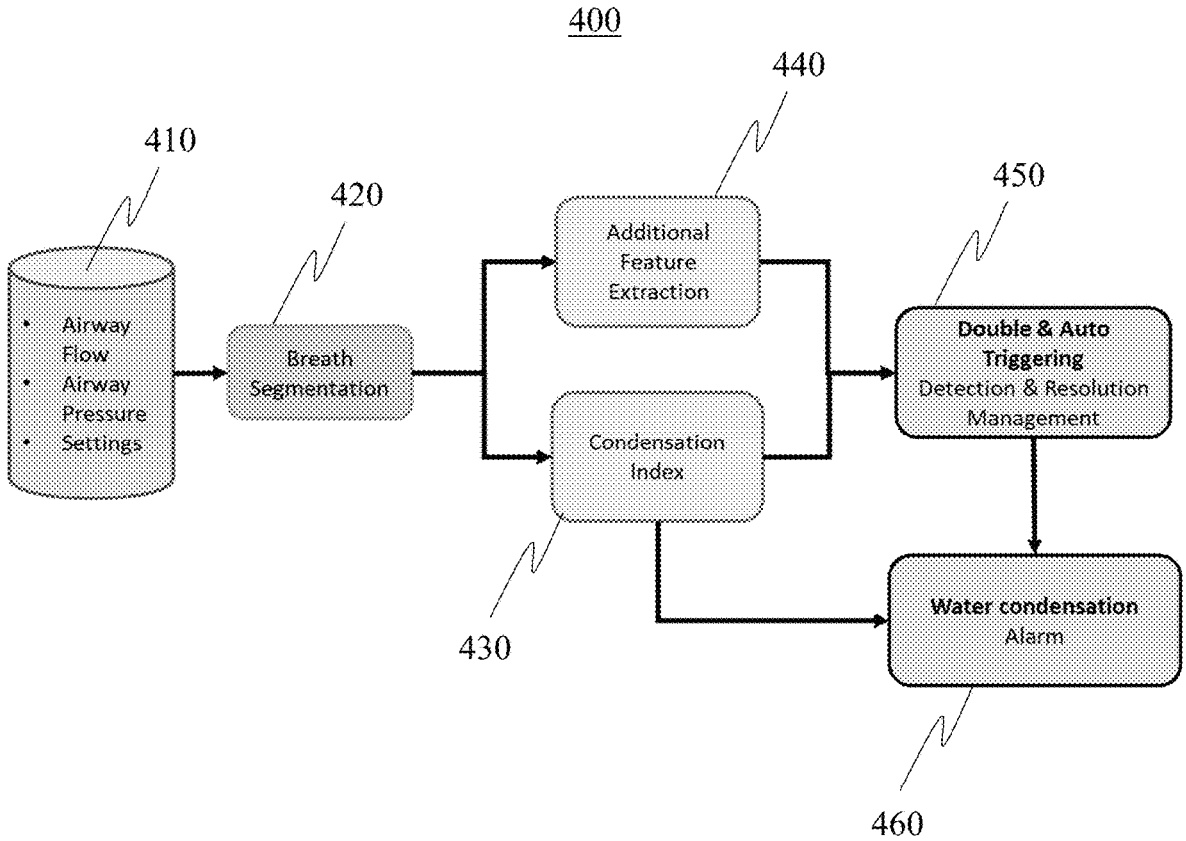
FIG. 4 is a flowchart of a method for automated detection of water accumulation in a ventilator, in accordance with an embodiment.

Referring to FIG. 4, in one embodiment, is a high-level overview 400 of a method 100 for automated detection of water accumulation in a ventilator circuit by a trained asynchrony detection algorithm of a ventilator system. The water accumulation index is one of many important and extracted features of the machine learning model for automated detection of double-triggering or auto-triggering asynchrony. Once the model detects asynchrony, the clinician is promptly alerted. If the detection or asynchrony is triggered due to a high water accumulation index value, appropriate cleaning (e.g., removal of water) of the airway circuit is recommended. Additionally, the water accumulation index itself can be used to trigger a water accumulation alarm in the absence of any detected asynchronies to minimize risk of infection and optimal operation of the ventilator and its components and accessories.

In FIG. 4, airway flow and airway pressure and/or one or more other features ("settings") 410 are utilized for breath segmentation 420, including generation of a water accumulation index ("condensation index") at 430. The airway flow and airway pressure and/or one or more other features ("settings") 410 can also be used to identify and/or extract one or more other features 440. A trained asynchrony detection algorithm utilizes the input 440 and 430 to determine whether there is double-triggering, auto-triggering, ineffective triggering, or another type of asynchrony 450, and/or whether there is water accumulation 460. The system can then alarm a user to the asynchrony and/or water accumulation.

Figure 2:
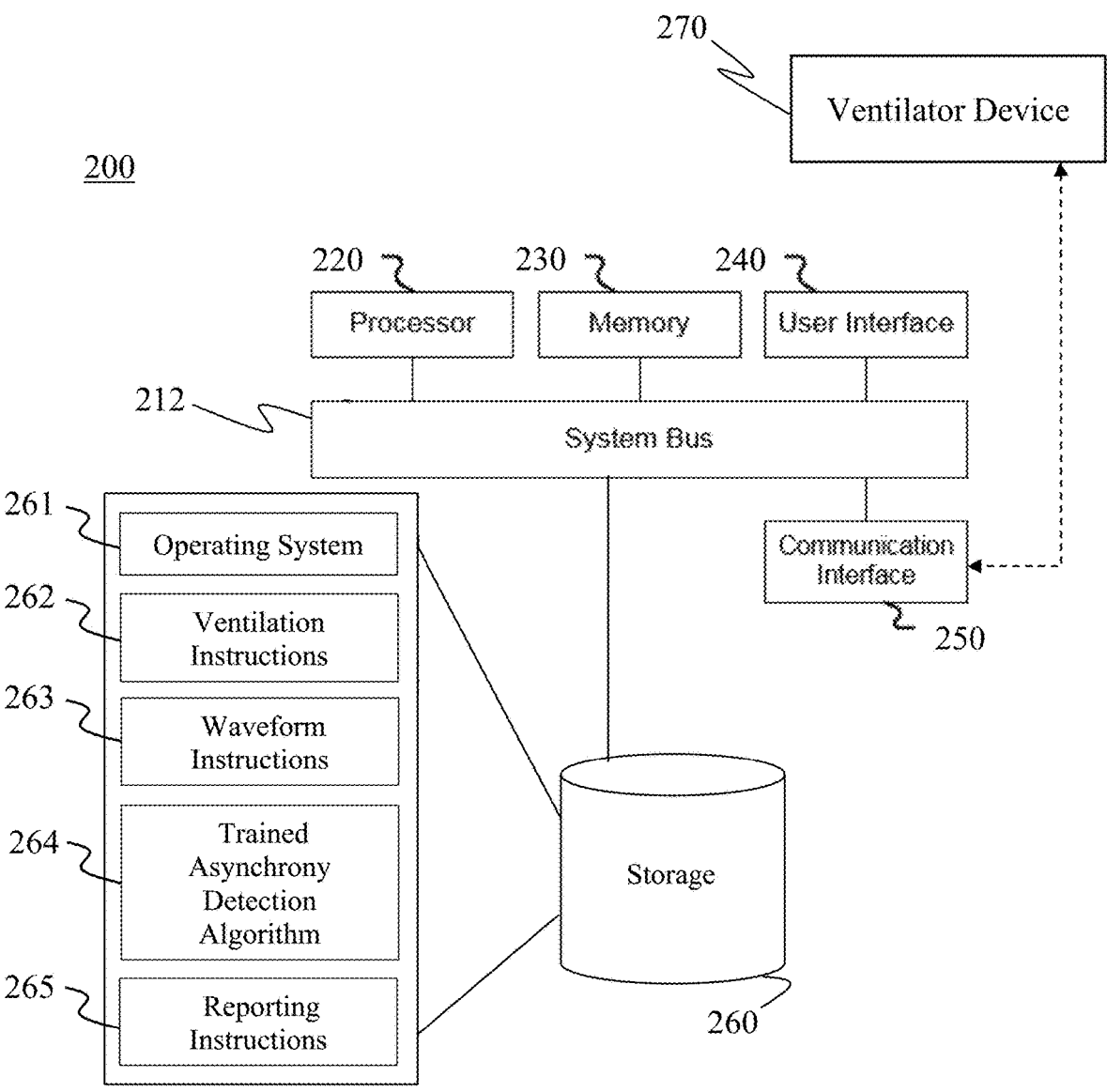
FIG. 2 is a schematic representation of a ventilator system, in accordance with an embodiment.

Returning to FIG. 1, at step 110 of the method, a ventilator system 200 is provided. Referring to an embodiment of a ventilator system 200 as depicted in FIG. 2, for example, the system comprises one or more of a processor 220, memory 230, user interface 240, communications interface 250, storage 260, and ventilator device 270, interconnected via one or more system buses 212. It will be understood that FIG. 2 constitutes, in some respects, an abstraction and that the actual organization of the components of the system 200 may be different and more complex than illustrated. Additionally, ventilator system 200 can be any of the systems described or otherwise envisioned herein. Other elements and components of system 200 are disclosed and/or envisioned elsewhere herein.

At step 120 of the method, the ventilator device 270 of the ventilator system 200 is utilized to ventilate a patient (not shown), and the ventilator system receives at least an airway pressure waveform and a flow waveform from the ventilator device for one or more breaths of the patient. The ventilator device 270 can be any device suitable to ventilate a patient for any reason requiring ventilation. The setting for the ventilator system can be a hospital setting, a nursing home setting, a long-term care setting, a home setting, and/or any other healthcare setting. One or more parameters of the ventilator device can be set, adjusted, preprogrammed, or otherwise determined by a healthcare professional.

According to an embodiment, the ventilator system receives or otherwise determines one or more other input features utilized as input by the trained asynchrony detection algorithm. Other examples of input features received by the ventilator system and utilized by the trained asynchrony detection algorithm include, but are not limited to, one or more of an estimate of cardiogenic artifact within the breath, ventilator settings (e.g., threshold value, control mode, positive end expiratory pressure (PEEP) level, etc.), ventilator breathing circuit (e.g., single limb, dual limb, mask . . . ), excursion of patient effort (i.e., area under the ventilator threshold when the breath is triggered), slope of the patient effort in the pressure and/or flow channel, patient effort lowest/highest value in the pressure and/or flow channel (including around breath initiation), estimation of patient effort in the airway pressure channel, estimation of patient effort in the flow channel, estimate of intrinsic PEEP level (i.e., baseline level—PEEP), and estimate of patient respiratory mechanics (i.e., respiratory compliance and/or resistance), among other possible input features.

Once the ventilator system receives, retrieves, or otherwise determines the airway pressure waveform, the flow waveform, and/or one or more additional input features from the ventilator system, this information can be utilized immediately or can be stored in local or remote storage for subsequent use.

At step 130 of the method, the ventilator system calculates an airway pressure water accumulation index from the received airway pressure waveform for a patient breath. The ventilator system can calculate the airway pressure water accumulation index using a variety of different methods, and optionally calculates the airway pressure water accumulation index on a breath-by-breath basis. According to an embodiment, the ventilator system calculates the airway pressure water accumulation index on a breath-by-breath basis using the past one second of waveform data, although other timeframes and windows are possible.

Figure 5:
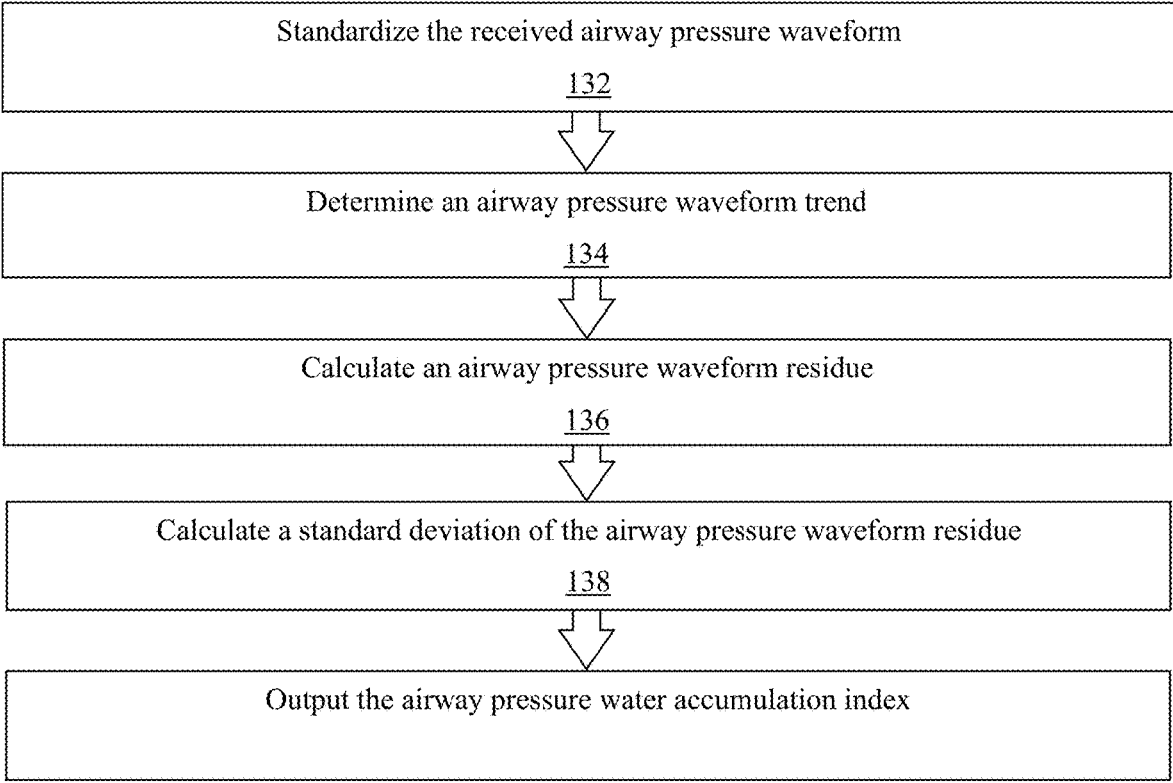
FIG. 5 is a flowchart of a method for calculating an airway pressure water accumulation index, in accordance with an embodiment.

Referring to FIG. 5, in one embodiment, is a method 500 for calculating an airway pressure water accumulation index from a received airway pressure waveform for a patient breath. At step 132 of method 500, the received airway pressure waveform is standardized so that there are zero mean and unit variance. According to an embodiment, standardizing the received airway pressure waveform comprises subtracting a calculated airway pressure waveform mean and dividing the received airway pressure waveform by a calculated standard deviation of the airway pressure waveform.

At step 134 of the method, the ventilator system determines an airway pressure waveform trend, comprising application of a median filter. The filter may utilize a variety of different sample sizes. According to an embodiment, the medial filter is applied with a kernel of size three samples (e.g., for waveforms sampled at 100 Hz).

At step 136 of the method, the ventilator system calculates an airway pressure waveform residue, comprising subtracting the determined waveform trend from the standardized airway pressure waveform for the breath.

At step 138 of the method, the ventilator system calculates a standard deviation of the computed airway pressure waveform residue. This comprises the final water accumulation index for the airway pressure waveform for the breath. Once it is determined, the airway pressure water accumulation index may be utilized immediately or may be stored in local or remote storage for subsequent use in the method.

At step 140 of the method, the ventilator system calculates a flow water accumulation index from the received flow waveform for a patient breath. The ventilator system can calculate the flow water accumulation index using a variety of different methods, and optionally calculates the flow water accumulation index on a breath-by-breath basis. According to an embodiment, the ventilator system calculates the flow water accumulation index on a breath-by-breath basis using the past one second of waveform data, although other timeframes and windows are possible.

Notably, according to an embodiment, steps 130 and 140 of the method are completed sequentially in any order, or the steps are completed in parallel.

Figure 6:
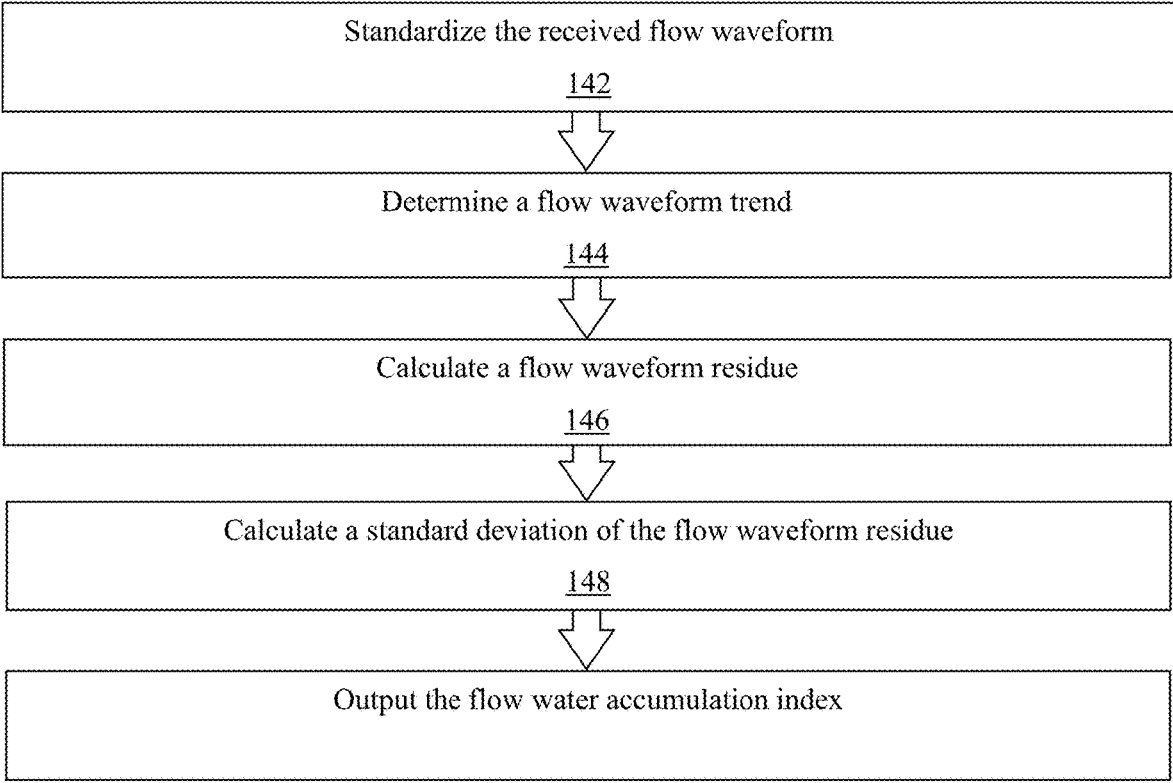
FIG. 6 is a flowchart of a method for calculating flow water accumulation index, in accordance with an embodiment.

Referring to FIG. 6, in one embodiment, is a method 600 for calculating a flow water accumulation index from a received flow waveform for a patient breath. At step 142 of method 600, the received flow waveform is standardized so that there are zero mean and unit variance. According to an embodiment, standardizing the received flow waveform comprises subtracting a calculated flow waveform mean and dividing the received flow waveform by a calculated standard deviation of the flow waveform. However, other methods for standardizing the received flow waveform are possible. For example, according to another embodiment, standardizing the received flow waveform comprises subtracting a calculated flow waveform median and dividing the received flow waveform by a calculated standard deviation of the flow waveform. Many other methods are possible.

At step 144 of the method, the ventilator system determines a flow waveform trend, comprising application of a median filter. The filter may utilize a variety of different sample sizes. According to an embodiment, the medial filter is applied with a kernel of size three samples (e.g., for waveforms sampled at 100 Hz).

At step 146 of the method, the ventilator system calculates a flow waveform residue, comprising subtracting the determined waveform trend from the standardized flow waveform for the breath.

At step 148 of the method, the ventilator system calculates a standard deviation of the computed flow waveform residue. This comprises the final water accumulation index for the flow waveform for the breath. Once it is determined, the flow water accumulation index may be utilized immediately or may be stored in local or remote storage for subsequent use in the method.

Figure 7:
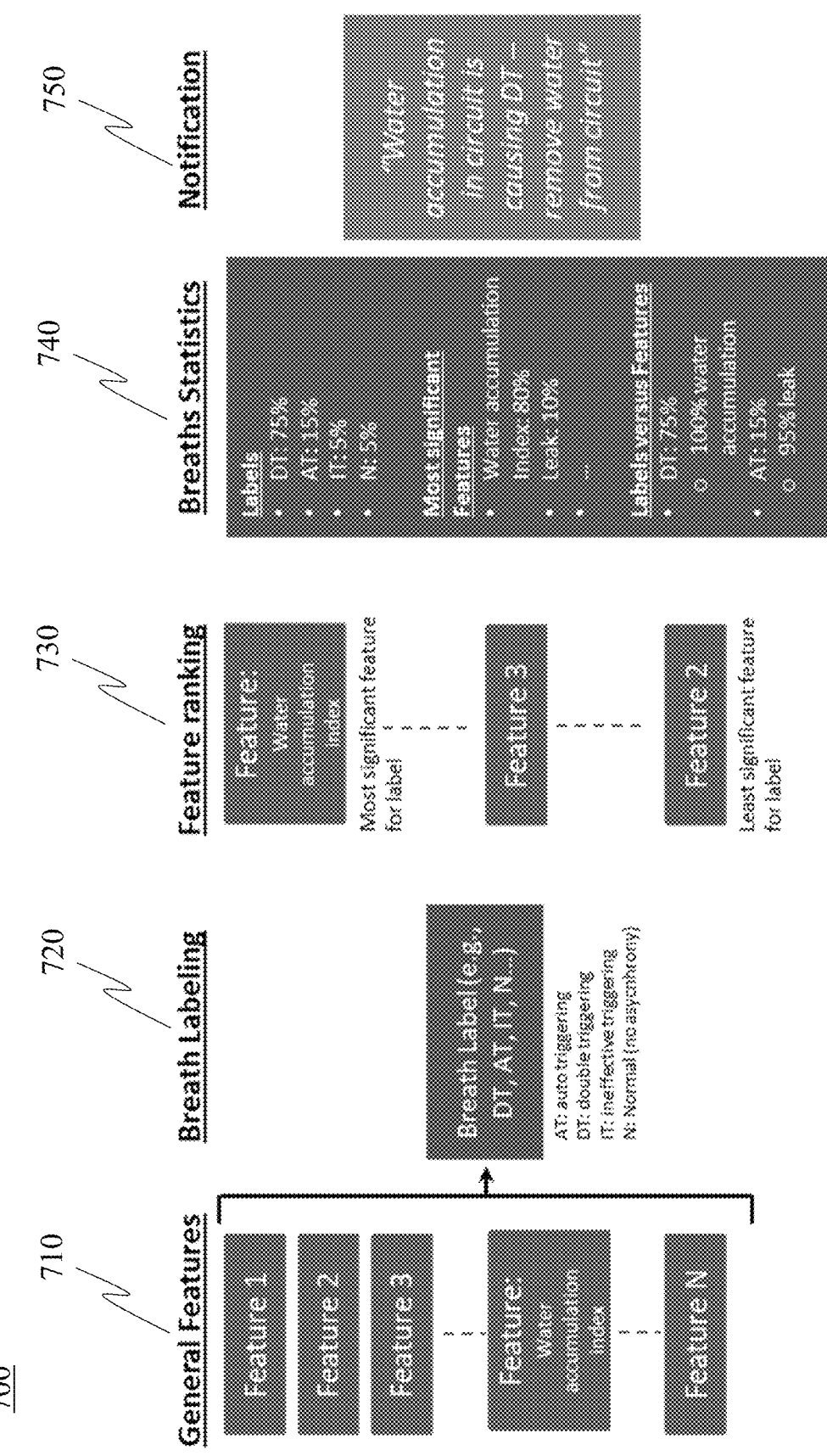
FIG. 7 is a flowchart of a method for automated detection of water accumulation in a ventilator, in accordance with an embodiment.

Referring to FIG. 7, in one embodiment, is another high-level overview 700 of a method 100 for automated detection of water accumulation in a ventilator circuit by a trained asynchrony detection algorithm of a ventilator system. At step 710, the input features for the trained asynchrony detection algorithm are determined or received. For example, the input features (feature 1, feature 2, . . . feature N) comprises at least the airway pressure water accumulation index and the flow water accumulation index, although the input features may comprise one or more additional input features.

Returning to FIG. 1, at step 150 of the method, the trained asynchrony detection algorithm of the ventilator system labels or otherwise identifies a single breath of the patient as synchronous or asynchronous. The trained asynchrony detection algorithm utilizes at least the airway pressure water accumulation index and the flow water accumulation index as input features, although the input features utilized by the trained asynchrony detection algorithm may comprise one or more additional input features. This label can be utilized immediately or can be stored in local or remote storage for subsequent use in the method.

According to an embodiment, the trained asynchrony detection algorithm of the ventilator system further labels or otherwise identifies the single breath of the patient as asynchronous and identifies that asynchrony as auto-triggered, double-triggered, or ineffectively triggered. Other types of asynchrony are possible.

According to an embodiment, the trained asynchrony detection algorithm can be any machine learning algorithm, classifier, or model sufficient to utilize the input features described or otherwise envisioned herein, and sufficient to label or otherwise identify a single breath of the patient as synchronous or asynchronous. According to an embodiment, the trained asynchrony detection algorithm is trained by the ventilator system. According to another embodiment, the trained asynchrony detection algorithm is trained by another system.

According to an embodiment, an asynchrony detection algorithm can be trained using breath-by-breath input feature such as airway pressure water accumulation index and the flow water accumulation index (along the other features) along with ground truth or other training data in order to be trained to predict or detect asynchronies, and label asynchronies as auto-triggered, double-triggered, or ineffectively triggered. Standard machine learning models can be used to train the asynchrony detection classifier. Training the asynchrony detection algorithm may comprise, for example, optimizing the kernel size, and/or exploring spectral approaches such as ratio of the first harmonic to the rest of the spectrum as a measure of high frequency content. According to one specific, non-limiting example, an asynchrony detection algorithm can be a Lasso model with 5-fold cross validation using a plurality of breaths from clinical and/or mechanical lab datasets.

Referring again to the high-level overview 700 of method 100 for automated detection of water accumulation in a ventilator circuit, at step 720 the trained asynchrony detection algorithm of the ventilator system labels or otherwise identifies the patient's breath as synchronous (e.g., "normal" or "no asynchrony") or as asynchronous (e.g., auto-triggered (AT), double-triggered (DT), ineffectively triggered (IT), or another type of asychrony).

Returning to FIG. 1, at step 160 of the method, the trained asynchrony detection algorithm of the ventilator system ranks the plurality of input features in a ranked order, where the ranked order is based on an importance of each respective input feature to the determination of the single breath of the patient as synchronous or asynchronous by the trained asynchrony detection algorithm. Accordingly, the asynchrony detection algorithm of the ventilator system is further trained to determine the importance of each input feature to the output of the algorithm (i.e., the labeling of the single breath of the patient as synchronous or asynchronous), and to rank the input features according to that determined importance. The ranking therefore comprises at least a determination of a most important input feature.

As described or otherwise envisioned herein, the plurality of input features comprises at least the airway pressure water accumulation index and the flow water accumulation index as input features, although the plurality of input features may comprise one or more additional input features. Accordingly, the ranking may be a ranked order of at least the airway pressure water accumulation index and the flow water accumulation index.

Once the ranking of the plurality of input features and the determination of the most important input feature for the patient breath is determined, this output can be utilized immediately or can be stored in local or remote storage for subsequent use.

Referring again to the high-level overview 700 of method 100 for automated detection of water accumulation in a ventilator circuit, at step 730 the trained asynchrony detection algorithm of the ventilator system ranks the input features based on importance of the feature on the determination of synchronous or asynchronous for the patient breath. For example, in FIG. 7 the water accumulation index is the most important input feature for that patient breath, followed by input feature three and then by input feature two.

According to an embodiment, multiple iterations of steps 120 through 160 are completed, one iteration each for each of a plurality of a patient's breaths. These plurality of breaths may be a plurality of or all consecutive breaths in a predetermined window or timeframe, or may be sampled non-consecutive breaths within a predetermined window or timeframe. The predetermined window or timeframe may be a setting of the ventilator system, a preprogrammed default, a variable predetermined window or timeframe determined by a parameter of the patient, the ventilator, and/or one or more ventilator settings, among other possibilities.

At step 170 of the method, the trained asynchrony detection algorithm of the ventilator system utilizes data from a plurality of iterations of step 120 through 160, thus data for a plurality of a patient's breaths, to determine several different parameters. As one determined parameter, the system determines a most frequent breath labeling for the plurality of iterations, wherein the most frequent breath labeling is one of synchronous (N), auto-triggered (AT), double-triggered (DT), ineffectively triggered (IT), or another type of asychrony. According to one possible embodiment, determining a most frequent breath labeling for the plurality of iterations comprises determining, for the plurality of iterations, a percentage of each of the synchronous, auto-triggered, double-triggered, ineffectively triggered, or other type of asychrony breath labels relative to all labels.

For example, referring to step 740 in FIG. 7, determining a most frequent breath labeling for the plurality of iterations comprises determining the percentage of synchronous (N 5%), auto-triggered (AT 15%), double-triggered (DT 75%), or ineffectively triggered (IT 5%) breath labels relative to all labeled breaths (100%).

According to an embodiment, as another determined parameter, the system determines a most frequent most important input feature for the plurality of iterations. According to one possible embodiment, determining a most frequent most important input feature for the plurality of iterations comprises determining, for the plurality of iterations, a percentage of iterations each of the input features is most important to the determination by the trained asynchrony detection algorithm.

For example, referring to step 740 in FIG. 7, determining a most frequent most important input feature for the plurality of iterations comprises determining that the water accumulation index was the most frequent most important input feature (80% of the iterations), while leak was the second most frequent most important input feature (10% of the iterations), and one or more other input features were the most important input feature the remaining percentage of the iterations (10%).

According to an embodiment, as another determined parameter, the system determines a most frequent most important input feature for each of the synchronous, auto-triggered, double-triggered, and ineffectively triggered breath labels. According to one possible embodiment, determining a most frequent most important input feature for each of the synchronous, auto-triggered, double-triggered, and ineffectively triggered breath labels comprises determining a percentage of the most important input feature for each of the breath labels.

For example, referring to step 740 in FIG. 7, determining a most frequent most important input feature for each of the synchronous, auto-triggered, double-triggered, and ineffectively triggered breath labels comprises determining that for the double-triggered (DT) breath labels (which was 75% of the breath labels as determined by the trained asynchrony detection algorithm above), the most frequent most important input feature was water accumulation which was 100% of the time. For auto-triggered (AT) breath labels (which was 15% of the breath labels as determined by the trained asynchrony detection algorithm above), the most frequent most important input feature was leak which was 95% of the time.

According to an embodiment, once the most frequent breath labeling for the plurality of iterations, the most frequent most important input feature for the plurality of iterations, and the most frequent most important input feature for each of the synchronous, auto-triggered, double-triggered, and ineffectively triggered breath labels are determined, these parameters may be utilized immediately or may be stored in local or remote storage for subsequent use in the method.

Thus, according to an embodiment, information provided to the user is be divided into three levels: (i) a ranked list of labels with the corresponding percentage of occurrence (frequency) (e.g., 75% DT, 15% AT . . . ); (ii) a ranked list of features with the corresponding percentage of times they ranked highest in importance (e.g., water accumulation index ranked highest 80% of all breaths); and (iii) a ranking of features by importance and provided label by label to relate the root cause of asynchrony. For example, as shown in FIG. 7, DT occurred in 75% of the breaths, and in all of those breaths the highest-ranking feature was the water accumulation index. Thus, in this case DT was mainly caused by water accumulation. Notably, there can be cases where DT is caused by another major reason or there is no asynchrony but still there is water accumulation. TABLE 1 identifies several of these differences and how they affect the notifications.

Referring to TABLE 1 are several case examples. According to an embodiment, the trained asynchrony detection algorithm can capture root causes of asynchrony (i.e., if water accumulation is a root cause) but at the same time can protect a user from incorrect conclusions. For example, DT can be high and water accumulation could be present; however, it might not be the major reason for DT. For example, in case 2 even though there is no asynchrony water accumulation still exists because the water accumulation index is still ranked high in these features, or its value exceeds a certain threshold determined by the algorithm. In case 3, water accumulation exists but it is not causing the DT. While in Case 4, DT is specifically caused by the water collection.

TABLE 1

| | | Water accumulation index ranking for N | | Water accumulation index ranking for DT | |
|---|---|---|---|---|---|
| | N | | DT | | Notification on water accumulation index |
| Case 1 | ↑ | ↓ | ↓ | ↓ | No water accumulation in circuit. No actions needed. |
| Case 2 | ↑ | ↑ | ↓ | ↓ | Water accumulation detected - remove water from circuit |
| Case 3 | ↑ | ↑ | ↑ | ↓ | Water accumulation detected - remove water from circuit. DT detected but caused by Feature X (not water accumulation) |

Case Examples

TABLE 1-continued

| | | | | | |
|---|---|---|---|---|---|
| | | Water accumulation index ranking | | Water accumulation index ranking | Notification on water |
| | N | for N | DT | for DT | accumulation index |
| Case 4 | ↓ | ↓ | ↑ | ↑ | Water accumulation causing DT-remove water from circuit to reduce DT |

N: normal breaths,
DT: double triggering breaths

Returning to method 100 in FIG. 1, at step 180 the trained asynchrony detection algorithm utilizes the determined parameters (e.g., the most frequent breath labeling for the plurality of iterations, the most frequent most important input feature for the plurality of iterations, and the most frequent most important input feature for each of the synchronous, auto-triggered, double-triggered, and ineffectively triggered breath labels) to determine one or more of: (i) water accumulation in the ventilator circuit and an action to remove the water accumulation from the ventilator circuit; and (ii) asynchrony in the ventilator circuit due to a cause other than water accumulation, and an action to correct the asynchrony.

According to an embodiment, therefore, the asynchrony detection algorithm is further trained to determine, from the provided parameters, whether there is water accumulation in the ventilator circuit. The asynchrony detection algorithm is further trained to determine, from the provided parameters, what action should be taken to remove the water accumulation from the ventilator circuit, or what action should be taken if there is asynchrony in the ventilator circuit due to a cause other than water accumulation.

Once the trained asynchrony detection algorithm utilizes the determined parameters to identify water accumulation and/or asynchrony as well as an action to take, this information may be utilized immediately or can be stored in local or remote storage for subsequent use in the method.

Referring again to the high-level overview 700 of method 100 for automated detection of water accumulation in a ventilator circuit, at step 750 the trained asynchrony detection algorithm of the ventilator system has determined that water accumulation is causing double-triggering (DT) and has determined an action to take to correct the situation ("remove water from circuit").

Returning to method 100 in FIG. 1, at step 190 of the method, the ventilation system displays or otherwise provides one or both of: (i) the determination of water accumulation in the ventilator circuit and/or the determination of asynchrony due to a reason other than water accumulation; and (ii) the action determined to correct the water accumulation and/or asynchrony, using a user interface 240 of the ventilator system 200. The user interface may be any method or component sufficient to communicate the information to a user. According to an embodiment, the system may display a report on the user interface or display of the system, or may issue an alarm. The information may be communicated by wired and/or wireless communication to another device. For example, the system may communicate the report to a mobile phone, computer, laptop, wearable device, and/or any other device configured to allow display and/or other communication of the report.

Referring again to the high-level overview 700 of method 100 for automated detection of water accumulation in a ventilator circuit, at step 750 the trained asynchrony detection algorithm of the ventilator system has determined that water accumulation is causing double-triggering (DT) and has determined an action to take to correct the situation ("remove water from circuit"), and this information is communicated to the user via a user interface.

Referring again to FIG. 2 is a schematic representation of a ventilation system 200. System 200 may be any of the systems described or otherwise envisioned herein, and may comprise any of the components described or otherwise envisioned herein. It will be understood that FIG. 2 constitutes, in some respects, an abstraction and that the actual organization of the components of the system 200 may be different and more complex than illustrated.

According to an embodiment, system 200 comprises a processor 220 capable of executing instructions stored in memory 230 or storage 260 or otherwise processing data to, for example, perform one or more steps of the method. Processor 220 may be formed of one or multiple modules. Processor 220 may take any suitable form, including but not limited to a microprocessor, microcontroller, multiple microcontrollers, circuitry, field programmable gate array (FPGA), application-specific integrated circuit (ASIC), a single processor, or plural processors.

Memory 230 can take any suitable form, including a non-volatile memory and/or RAM. The memory 230 may include various memories such as, for example L1, L2, or L3 cache or system memory. As such, the memory 230 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 200. It will be apparent that, in embodiments where the processor implements one or more of the functions described herein in hardware, the software described as corresponding to such functionality in other embodiments may be omitted.

User interface 240 may include one or more devices for enabling communication with a user. The user interface can be any device or system that allows information to be conveyed and/or received, and may include a display, a mouse, and/or a keyboard for receiving user commands. In some embodiments, user interface 240 may include a command line interface or graphical user interface that may be presented to a remote terminal via communication interface 250. The user interface may be located with one or more other components of the system, or may be located remote from the system and in communication via a wired and/or wireless communications network.

Communication interface 250 may include one or more devices for enabling communication with other hardware devices. For example, communication interface 250 may include a network interface card (NIC) configured to communicate according to the Ethernet protocol. Additionally, communication interface 250 may implement a TCP/IP stack for communication according to the TCP/IP protocols. Various alternative or additional hardware or configurations for communication interface 250 will be apparent.

Storage 260 may include one or more machine-readable storage media such as read-only memory (ROM), random-access memory (RAM), magnetic disk storage media, optical storage media, flash-memory devices, or similar storage media. In various embodiments, storage 260 may store instructions for execution by processor 220 or data upon which processor 220 may operate. For example, storage 260 may store an operating system 261 for controlling various operations of system 200.

It will be apparent that various information described as stored in storage 260 may be additionally or alternatively stored in memory 230. In this respect, memory 230 may also be considered to constitute a storage device and storage 260 may be considered a memory. Various other arrangements will be apparent. Further, memory 230 and storage 260 may both be considered to be non-transitory machine-readable media. As used herein, the term non-transitory will be understood to exclude transitory signals but to include all forms of storage, including both volatile and non-volatile memories.

While system 200 is shown as including one of each described component, the various components may be duplicated in various embodiments. For example, processor 220 may include multiple microprocessors that are configured to independently execute the methods described herein or are configured to perform steps or subroutines of the methods described herein such that the multiple processors cooperate to achieve the functionality described herein. Further, where one or more components of system 200 is implemented in a cloud computing system, the various hardware components may belong to separate physical systems. For example, processor 220 may include a first processor in a first server and a second processor in a second server. Many other variations and configurations are possible.

According to an embodiment, storage 260 of system 200 may store one or more algorithms, modules, and/or instructions to carry out one or more functions or steps of the methods described or otherwise envisioned herein. For example, the system may comprise, among other instructions or data, ventilation instructions 262, waveform instructions 263, a trained asynchrony algorithm 264, and/or reporting instructions 265, among many other possible instructions and/or data.

According to an embodiment, ventilation instructions 262 direct the system to operate the ventilator device 270 of the ventilation system 200, specifically to ventilate a patient. The ventilator device can be any device suitable to ventilate a patient for any reason requiring ventilation. One or more parameters of the ventilator device instructions can be set, adjusted, preprogrammed, or otherwise determined by a healthcare professional. Thus, the ventilation instructions 262 enable operation of the ventilation device to ventilate the patient.

According to an embodiment, waveform instructions 263 direct the system to calculate an airway pressure water accumulation index from the received airway pressure waveform for a patient breath, and a flow water accumulation index from the received flow waveform for a patient breath. The ventilator system can calculate the airway pressure water accumulation index and the flow water accumulation index using a variety of different methods, and optionally calculates these indexes on a breath-by-breath basis. According to an embodiment, the ventilator system calculates the airway pressure water accumulation index and the flow water accumulation index using the methods described in conjunction with method 500 in FIG. 5 and method 600 in FIG. 6, although other methods are possible.

According to an embodiment, the trained asynchrony algorithm 264 is trained to utilize the input features described or otherwise envisioned herein, in order to generate the one or more outputs described or otherwise envisioned herein. According to an embodiment, the trained asynchrony detection algorithm can be any machine learning algorithm, classifier, or model sufficient to utilize the input features described or otherwise envisioned herein, and sufficient to label or otherwise identify a single breath of the patient as synchronous or asynchronous. According to an embodiment, the trained asynchrony detection algorithm is trained by the ventilator system. According to another embodiment, the trained asynchrony detection algorithm is trained by another system.

According to an embodiment, reporting instructions 265 direct the system to display or otherwise provide one or both of: (i) the determination of water accumulation in the ventilator circuit and/or the determination of asynchrony due to a reason other than water accumulation; and (ii) the action determined to correct the water accumulation and/or asynchrony, using the user interface 240 of the ventilator system 200. The report or display can comprise any of the information described or otherwise envisioned herein, including but not limited to the determination of water accumulation in the ventilator circuit and/or the determination of asynchrony due to a reason other than water accumulation, the action determined to correct the water accumulation and/or asynchrony, any of the parameters or percentages or rankings determined or analyzed by the ventilator system, any information about the patient, and/or any other information. The user interface may be any method or component sufficient to communicate the information to a user. According to an embodiment, the instructions may direct the system to display the information on the user interface or display of the system. According to an embodiment, the information may be communicated by wired and/or wireless communication to another device. For example, the system may communicate the report to a mobile phone, computer, laptop, wearable device, and/or any other device configured to allow display and/or other communication of the information.

Non-Limiting Example

Described below is a non-limiting example of a trained asynchrony algorithm of a ventilation system being trained with input features to generate an output. This is just one possible approach and embodiment of the methods and systems described or otherwise envisioned herein, and thus does not limit the scope of these methods and systems.

According to this example, an asynchrony algorithm is a Lasso model with 5-fold cross validation, using 8,167 breaths from both clinical and mechanical lab datasets as training data. For checking the water accumulation index separately on both pressure and flow waveforms, the classifier was trained on only these two measurements. Using these two features alone, the system was able to achieve Area Under the Receiver Operating Curve (AUROC) of 62% and 76% for Pressure and Flow water accumulation indices respectively, as shown in TABLE 2. This is significantly higher than chance and provides evidence of its utility for the system, which when combined with all other features, achieves performance levels above 80%.

Referring to TABLE 2 is a summary of the analysis of a trained asynchrony algorithm. The algorithm achieves a performance significantly higher than chance in the detection of auto-triggering, signifying its utility. Py_residue_pow stands for the water accumulation index applied to the pressure waveform, and Flow_residue_pow stands for the water accumulation index applied to the flow waveform.

TABLE 2

|  | spearman corr with y | pearson corr with y | AUROC | AUPRC |
|---|---|---|---|---|
| py__residue__pow | −0.12 | −0.01 | 0.62 | 0.21 |
| flow__residue__pow | −0.26 | −0.28 | 0.76 | 0.25 |

Figure 8:
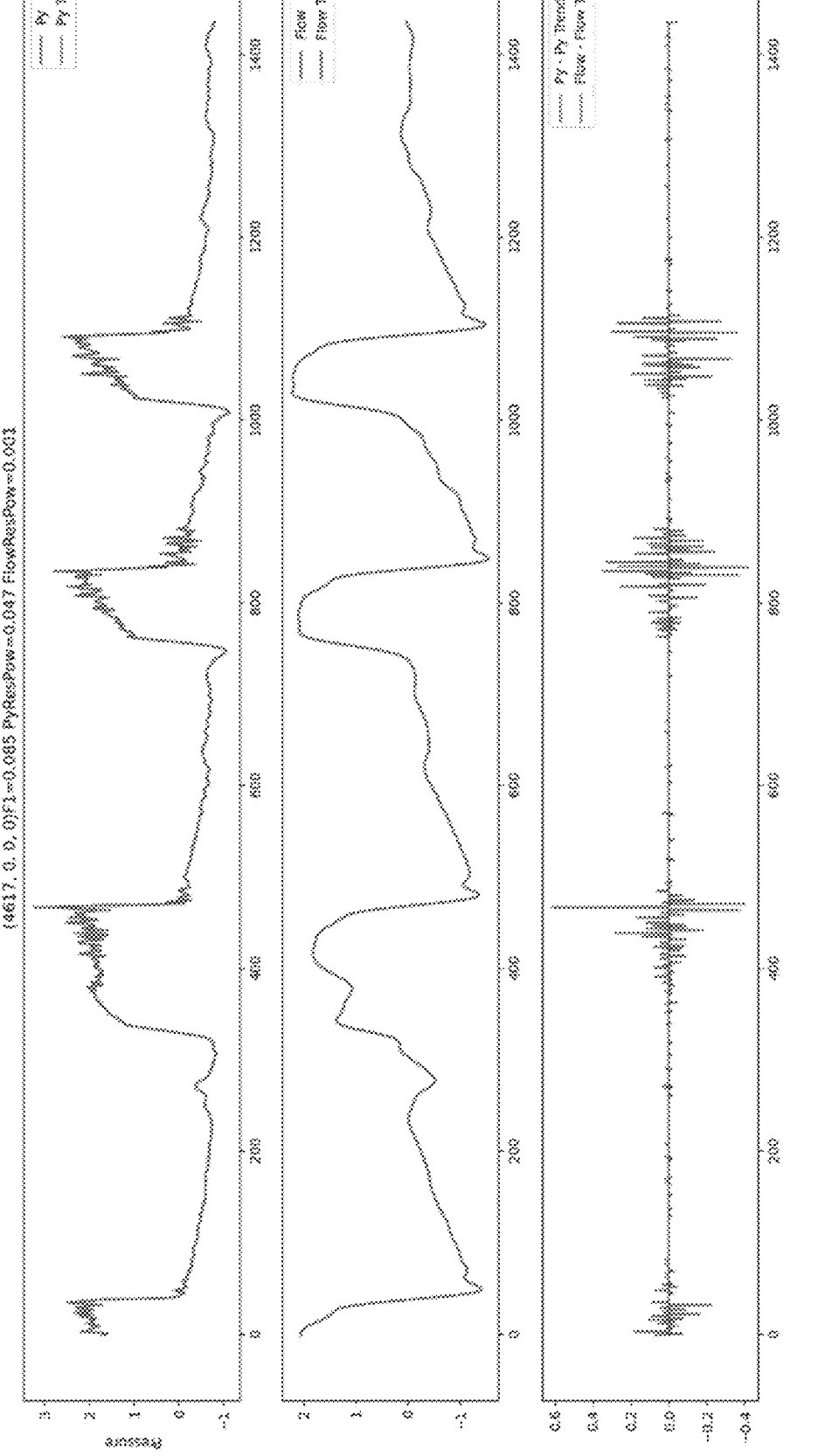
FIG. 8 is an example of calculation of water accumulation index, in accordance with an embodiment.

Referring to FIG. 8 is an example of calculation of water accumulation index. Airway Pressure (Py, top graph) and Flow (Flow, middle graph) are first standardized. A trend is then computed by applying a median filter with kernel size of 3 samples. The residue of the standardized waveforms are then calculated by subtracting the trend component from the standardized waveforms. Residues are shown on the bottom graph for the Pressure and Flow. The water accumulation index is the variance of these residue waveforms. The water accumulation index is lower in the Flow than in the Pressure because the Flow, in this case, is not affected.

Figure 9:
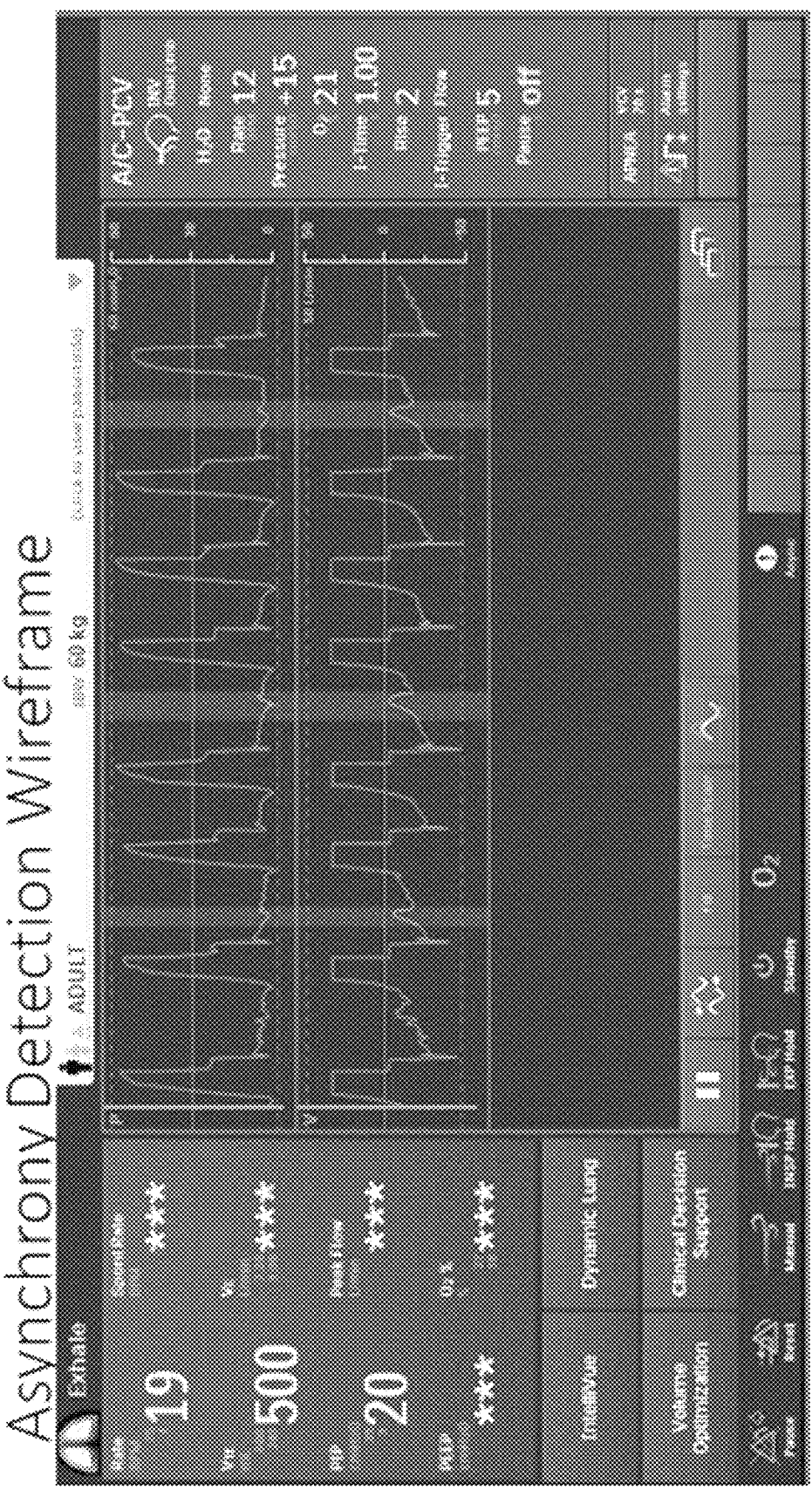
FIG. 9 is a schematic representation of a possible visualization of the ventilator system, in accordance with an embodiment.
Figure 10:
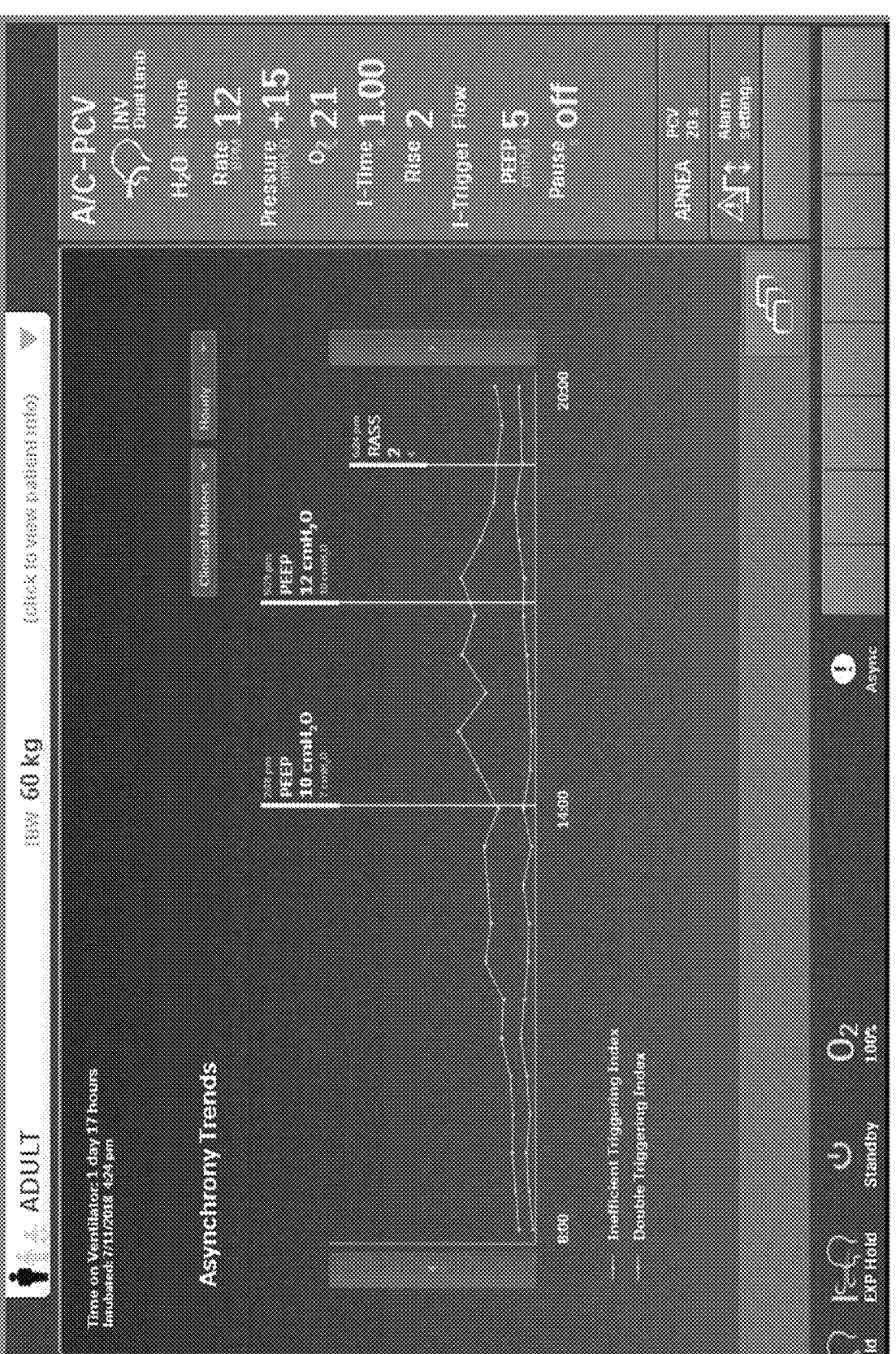
FIG. 10 is a schematic representation of a possible visualization of the ventilator system, in accordance with an embodiment.

Referring to FIGS. 9 and 10, in one embodiment, are possible visualizations or displays for the ventilation system 200, comprising one or more elements of the output of the system as described or otherwise envisioned herein. According to an embodiment, the methods and systems described or otherwise envisioned herein allows for significantly improved detection of asynchrony events based on physiological observations (i.e., noise in circuit based resulting from water accumulation). With accurate detection of asynchrony events including specifying their root cause (e.g., water accumulation), the system can report to healthcare providers breaths that are asynchronous as an alerts system in close to real-time, such as FIG. 9. Similarly, the system can also track and monitor long-term trends (e.g., 12 hours, 24 hours, 76 hours, etc.) superimposed on changes to the therapy so that the care giver can understand how asynchrony trends are affected by their actions, such as FIG. 10.

For example, in FIG. 9, the methods and systems described or otherwise envisioned herein enable the accurate detection and highlighting of patient ventilator asynchrony breaths on mechanical ventilators for review by a professional caregiver. If a high level of the water accumulation index contributed to the AI detection, then specific information related to water in the circuit can be displayed to the end user as actionable information.

For example, in FIG. 10, the methods and systems described or otherwise envisioned herein enable the collection of asynchrony event trends or the water accumulation index trend over large periods of care (e.g., 76 hours) and the display of those results superimposed on changes to patient care such as updates to ventilator settings or sedation levels. This new interface would give the caregiver insight as to possible causes for increases or decreases of asynchrony events over the course the therapy.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for automated detection of water accumulation in a ventilator device utilized to ventilate a patient, comprising:

a plurality of iterations of:

receiving, for a single breath of the patient, an airway pressure waveform and a flow waveform;

calculating, using the received airway pressure waveform, an airway pressure water accumulation index;

calculating, using the received flow waveform, a flow water accumulation index;

labeling, using at least the calculated airway pressure water accumulation index and the calculated flow water accumulation index as input features to a trained asynchrony detection algorithm, the single breath of the patient as synchronous or asynchronous, wherein an asynchronous breath is further labeled as auto-triggered, double-triggered, or ineffectively triggered; and ranking, by the trained asynchrony detection algorithm, all of the input features based on an importance of each respective input feature to the determination of the single breath of the patient as synchronous or asynchronous by the trained asynchrony detection algorithm, comprising at least a determination of a most important input feature;

for the plurality of iterations;

determining, by the trained asynchrony detection algorithm: (i) a most frequent breath labeling for the plurality of iterations, wherein the most frequent breath labeling is one of synchronous, auto-triggered, double-triggered, or ineffectively triggered, and (ii) a most frequent most important input feature for the plurality of iterations; and (iii) a most frequent most important input feature for each of the synchronous, auto-triggered, double-triggered, and ineffectively triggered breath labels; and determining, by the trained asynchrony detection algorithm using the most frequent breath labeling for the plurality of iterations, the most frequent most important input feature for the plurality of iterations, and the most frequent most important input feature for each of the synchronous, auto-triggered, double-triggered, and ineffectively triggered breath labels, one or more of: (i) water accumulation in the ventilator device and an action to remove the water accumulation from the ventilator device; and (ii)

asynchrony in the ventilator device due to a cause other than water accumulation, and an action to correct the asynchrony;

notifying, a user via a user interface of the ventilator device, of the determined action to remove the water accumulation from the ventilator device or the determined action to correct the asynchrony.

2. The method of claim 1, wherein said receiving step further comprises receiving at least one additional input feature from the ventilator device, and wherein labeling the single breath of the patient as synchronous or asynchronous further comprises using the received at least one additional input feature by the trained asynchrony detection algorithm.

3. The method of claim 2, wherein the at least one additional input feature from the ventilator device comprises one or more of an estimate of cardiogenic artifact within a breath, a ventilator setting, excursion of patient effort, slope of patient effort in a pressure and/or flow channel, patient effort lowest or highest value in a pressure and/or flow channel, estimation of patient effort in an airway pressure channel, estimation of patient effort in a flow channel, and estimate of intrinsic PEEP level.

4. The method of claim 1, wherein the determined action to remove the water accumulation from the ventilator device or the determined action to correct the asynchrony is removal of accumulated water from the ventilator device.

5. The method of claim 1, wherein the trained asynchrony detection algorithm determines water accumulation in the ventilator device, and the action to remove the water accumulation from the ventilator device, in the absence of asynchronous breaths of the patient.

6. The method of claim 1, wherein:

determining the most frequent breath labeling for the plurality of iterations comprises determining, for the plurality of iterations, a percentage of each of the synchronous, auto-triggered, double-triggered, or ineffectively triggered breath labels; and determining the most frequent most important input feature for the plurality of iterations comprises determining, for the plurality of iterations, a percentage of each of the input features.

7. The method of claim 1, wherein calculating the airway pressure water accumulation index comprises:

standardizing the received airway pressure waveform;

determining a waveform trend, comprising application of a median filter;

computing an airway pressure waveform residue, comprising subtracting the determined waveform trend from the standardized airway pressure waveform;

computing a standard deviation of the computed airway pressure waveform residue.

8. The method of claim 1, wherein calculating the flow water accumulation index comprises:

standardizing the received flow waveform, comprising subtracting a calculated flow waveform mean and dividing the received flow waveform by a calculated standard deviation of the flow waveform;

determining a waveform trend, comprising application of a median filter;

computing a flow waveform residue, comprising subtracting the determined waveform trend from the standardized flow waveform; and computing a standard deviation of the computed flow waveform residue.

9. A system for automated detection of water accumulation, comprising:

a ventilator device utilized to ventilate a patient, the ventilator device configured to provide an airway pressure waveform and a flow waveform for a single breath of the patient;

a trained asynchrony detection algorithm;

a processor configured to: (i) perform multiple iterations of: calculating, using the received airway pressure waveform, an airway pressure water accumulation index; calculating, using the received flow waveform, a flow water accumulation index; labeling, using at least the calculated airway pressure water accumulation index and the calculated flow water accumulation index as input features to the trained asynchrony detection algorithm, the single breath of the patient as synchronous or asynchronous, wherein an asynchronous breath is further labeled as auto-triggered, double-triggered, or ineffectively triggered; and ranking, by the trained asynchrony detection algorithm, all of the input features based on an importance of each respective input feature to the determination of the single breath of the patient as synchronous or asynchronous by the trained asynchrony detection algorithm, comprising at least a determination of a most important input feature; and (ii) for the plurality of iterations: determine, by the trained asynchrony detection algorithm: (1) a most frequent breath labeling for the plurality of iterations, wherein the most frequent breath labeling is one of synchronous, auto-triggered, double-triggered, or ineffectively triggered, and (2) a most frequent most important input feature for the plurality of iterations; and (3) a most frequent most important input feature for each of the synchronous, auto-triggered, double-triggered, and ineffectively triggered breath labels; and determine, by the trained asynchrony detection algorithm using the most frequent breath labeling for the plurality of iterations, the most frequent most important input feature for the plurality of iterations, and the most frequent most important input feature for each of the synchronous, auto-triggered, double-triggered, and ineffectively triggered breath labels, one or more of: (1) water accumulation in the ventilator device and an action to remove the water accumulation from the ventilator device; and (2) asynchrony in the ventilator device due to a cause other than water accumulation, and an action to correct the asynchrony; and a user interface configured to provide the determined action to remove the water accumulation from the ventilator device or the determined action to correct the asynchrony.

10. The system of claim 9, wherein the ventilator device is further configured to provide at least one additional input feature, and wherein labeling the single breath of the patient as synchronous or asynchronous further comprises using the received at least one additional input feature by the trained asynchrony detection algorithm.

11. The system of claim 10, wherein the at least one additional input feature from the ventilator device comprises one or more of an estimate of cardiogenic artifact within a breath, a ventilator setting, excursion of patient effort, slope of patient effort in a pressure and/or flow channel, patient effort lowest or highest value in a pressure and/or flow channel, estimation of patient effort in an airway pressure channel, estimation of patient effort in a flow channel, and estimate of intrinsic PEEP level.

12. The system of claim 9, wherein the determined action to remove the water accumulation from the ventilator device or the determined action to correct the asynchrony is removal of accumulated water from the ventilator device.

13. The system of claim 9, wherein the trained asynchrony detection algorithm determines water accumulation in the ventilator device, and the action to remove the water accumulation from the ventilator device, in the absence of asynchronous breaths of the patient.

14. The system of claim 9, wherein:

determining a most frequent breath labeling for the plurality of iterations comprises determining, for the plurality of iterations, a percentage of each of the synchronous, auto-triggered, double-triggered, or ineffectively triggered breath labels; and determining a most frequent most important input feature for the plurality of iterations comprises determining, for the plurality of iterations, a percentage of each of the input features.

15. The system of claim 9, wherein calculating the airway pressure water accumulation index or calculating the flow water accumulation index comprises:

standardizing the received waveform;

determining a waveform trend, comprising application of a median filter;

computing a waveform residue, comprising subtracting the determined waveform trend from the standardized waveform;

computing a standard deviation of the computed waveform residue.

* * * * *